(12) United States Patent
Baranowska-Kortylewicz et al.

(10) Patent No.: US 7,220,730 B2
(45) Date of Patent: May 22, 2007

(54) CANCER SPECIFIC RADIOLABELED CONJUGATES REGULATED BY THE CELL CYCLE FOR THE TREATMENT AND DIAGNOSIS OF CANCER

(75) Inventors: Janina Baranowska-Kortylewicz, Omaha, NE (US); Zbigniew Kortylewicz, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 185 days.

(21) Appl. No.: 10/671,376

(22) Filed: Sep. 25, 2003

(65) Prior Publication Data

US 2005/0069495 A1    Mar. 31, 2005

(51) Int. Cl.
*A61K 51/00* (2006.01)
*C07H 19/48* (2006.01)

(52) U.S. Cl. .................. 514/51; 514/50; 536/28.1; 534/11; 424/1.85; 424/1.73

(58) Field of Classification Search .............. 424/1.1, 424/1.85, 1.73; 436/504; 536/22.1, 28.1; 534/11; 514/50, 51
See application file for complete search history.

(56) References Cited

U.S. PATENT DOCUMENTS 5,096,694 A * 3/1992 Quivy et al. ............... 552/539
5,468,853 A 11/1995 Baranowska-Kortylewicz

FOREIGN PATENT DOCUMENTS

JP        1059990    * 3/1998
WO   WO 90/03799      4/1990

OTHER PUBLICATIONS

Downer, J.B. et al, Nuclear Medicine and Biology, 2001, 28, 613-626.*
Bonasera, T.A. et al. "Preclinical Evaluation of Fluorine-18-Labeled Androgen Receptor Ligands in Baboons"; Journal of Nuclear Medicine, 37(6): 1009-1015 (1996).
Choe, Y.S. et al. "Synthesis of 11β-[$^{18}$F]Fluro-5α-dihydrotestosterone and 11β-[$^{18}$F]Fluoro-19-nor-5α-dihydrotestosterone: Preparation via Halofluorination-Reduction, Receptor Binding, and Tissue Distribution"; Journal of Medicinal Chemistry, 38(5): 816-825 (1995).
Downer, J.B. et al. "Comparison of animal models for the evaluation of radiolabeled androgens"; Nuclear Medicine and Biology, 28(6): 613-626 (2001).
Hoyte, R.M. et al. "7α-Methyl-17α-(E-2'-[$^{125}$I]iodovinyl)-19-nortestosterone: a new radioligand for the detection of androgen receptor"; Steroids, 58(1): 13-23 (1993).
Labaree, D.C. et al. "7α-Iodine-125-Iodo-5α-Dihydrotestosterone: A Radiolabeled Ligand for the Androgen Receptor"; Journal of Nuclear Medicine, 38(3): 402-409 (1997).
Lara, P.N. et al. "Treatment Options in Androgen-Independent Prostate Cancer"; Cancer Investigation, 17(2): 137-144 (1999).
Liu, A. et al. "Fluorine-18-Labeled Androgens: Radiochemical Synthesis and Tissue Distribution Studies on Six Fluorine-Substituted Androgens, Potential Imaging Agents for Prostatic Cancer"; Journal of Nuclear Medicine, 33(5): 724-734 (1992).
Salman, M. et al. "A Potential Radioiodinated Ligand for Androgen Receptor: 7α-Methyl-17α-(2'-(E)-iodovinyl)-19-nortestosterone"; Journal of Medicinal Chemistry, 34(3): 1019-1024 (1991).
Van Den Bos, J.C., et al. "New Iodinated Progestins as Potential Ligands for Progesterone Receptor Imaging in Breast Cancer. Part 1: Synthesis and *in Vitro* Pharmacological Characterization"; Nuclear Medicine & Biology, 25(8): 781-789 (1998).
Warters, R.L. et al. "Radionuclide Toxicity in Cultured Mammalian Cells: Elucidation of the Primary Site of Radiation Damage"; Current Topics in Radiation Research Quarterly, 12: 389-407 (1997).
Makrigiorgos, G.M. et al. "Radiotoxicity of 5-[$^{123}$I]iodo-2'-deoxyuridine in V79 Cells: A Comparison with 5-[$^{125}$I]Iodo-2'-deoxyuridine"; Radiation Research, 118: 532 (1989).
Baranowska-Kortylewicz, J. et al. "5-[$^{123}$I]Iodo-2'-Deoxyuridine in the Radiotherapy of an Early Ascites Tumor Model"; Int. J. Radiat. Oncol. Biol. Phys., 21: 1541-1551 (1991).
Kyriakos, R.J. et al. "The Fate of Antibodies Bound to the Surface of Tumor Cells *in Vitro*"; Cancer Research, 52: 835-842 (1992).
Bryan, R.M. et al. "Androgen Receptors in Breast Cancer"; Cancer, 54: 2436-2440 (1984).
Lea, O.A. et al. "Improved Measurement of Androgen Receptors in Human Breast Cancer"; Cancer Research, 49: 7162-7167 (1989).
Soreide, J.A. et al. "Androgen receptors in operable breast cancer: relation to other steroid hormone receptors, correlations to prognostic factors and predictive value for effect of adjuvant tamoxifen treatment"; European Journal of Surgical Oncology, 18: 112-118 (1992).
Poulin, R. et al. "Androgens inhibit basal and estrogen-induced cell proliferation in the ZR-75-1 human breast cancer cell line"; Breast Cancer Research and Treatment, 12: 213-225 (1988).
Ingle, J.N. et al. "Combination Hormonal Therapy With Tamoxifen Plus Fluoxymesterone Versus Tamoxifen Alone in Postmenopausal Women With Metastatic Breast Cancer"; Cancer, 67: 886-891 (1991).
Mariani, G. et al. "Tumor Targeting Potential and Metabolism of 5-[$^{125}$I]Iodo-2'-Deoxyuridine Injected Intratumorally in Patients with Breast Cancer"; Ann N Y Acad. Sci., 698: 204-211 (1993).

* cited by examiner

*Primary Examiner*—Shaojia Anna Jiang
*Assistant Examiner*—Ganapathy Krishnan
(74) *Attorney, Agent, or Firm*—Dann, Dorfman, Herrell and Skillman, P.C.; Patrick J. Hagan (57) ABSTRACT

Radiolabeled conjugates are disclosed which have a component that is effective to target tumor cells, which cells selectively take up and degrade the conjugate, thereby delivering to the tumor cell nucleus a radioisotope capable of being incorporated into the nuclear material, so as to produce a cytotoxic effect and/or to render the cell detectable by radioimaging.

18 Claims, 5 Drawing Sheets

CANCER SPECIFIC RADIOLABELED CONJUGATES REGULATED BY THE CELL CYCLE FOR THE TREATMENT AND DIAGNOSIS OF CANCER

Pursuant to 35 U.S.C. Section 202(c), it is acknowledged that the United States Government has certain rights in the invention described herein, which was made in part with funds from the Department of Defense, Grant No. DAMD17-99-1-9313.

BACKGROUND OF THE INVENTION

The present invention relates generally to targeted therapy and medical imaging as applied to cancer treatment and diagnosis, and in particular to conjugates composed of a radiolabeled, cell cycle-dependent therapeutic agent chemically coupled to a ligand that targets androgen receptor (AR). The conjugates of the invention are taken up selectively by malignant tumor cells that have androgen receptor and are incorporated into the nucleus of such cells, where they produce a cytotoxic effect and/or are detectable via radioimaging techniques.

The main treatments for breast, prostate, ovarian and many other cancers are surgery, chemotherapy and radiation therapy. In some cases a combination of two or more of these treatments is recommended. Typically, clinical trials for advanced carcinomas use combination chemotherapy based on established anti-cancer agents. For example, there are numerous active clinical trials (Phase I) dealing with recurrent and progressive ovarian carcinoma that rely on existing drugs such as paclitaxel, carboplatin, cisplatin, floxouridine and similar drugs in a combination chemotherapy. Many of these include an autologous stem cell support to combat the side effects brought on by the administration of these drugs. Newer drugs include matrix metalloproteinase inhibitors, vaccines, and antibodies.

Many of the currently available front-line and salvage agents used in cancer therapy are associated with cumulative and/or irreversible toxicities that pose challenges for long-term treatment planning. The irreversible effects associated with some of these therapies include development of multidrug resistance, neurotoxicity, and nephrotoxicity. All of these diminish the probability of improved responses when multiple treatments are needed to keep the cancer under control.

It has previously been proposed to use targeted cytotoxic radioisotopes for the treatment and diagnosis of cancer. One of the intended benefits of targeted therapy is to diminish the incidence and severity of side effects by confining toxic exposure, more or less, to the disease site. Certain radioisotopes, particularly Auger electron-emitting isotopes, such as $^{123}$I and $^{125}$I are known to be very toxic to viable cells, but only if they are localized within the nucleus of the cell. (Warters et al., Curr. Top. Stop Rad. Res., 12:389 (1977).) It has been reported that 5'-iodo-2'-deoxyuridine (IUdR), when labeled with the Auger electron emitter $^{123}$I or $^{125}$I exhibits substantial toxicity in mammalian cells in vitro (Makrigiorgos et al., Radiat. Res., 118:532–44 (1989)) and produces a therapeutic effect in animal tumor models (Baranowska-Kortylewicz et al., Int. J. Radiat. Oncol. Biol. Phys., 21:1541–51 (1991)). Furthermore, radiolabeled IUdR has been found to enable scintigraphic detection of animal and human tumors (Baranowska-Kortylewicz, supra). See also U.S. Pat. Nos. 5,094,835 and 5,308,605.

Considerable effort has been devoted to developing antibodies for the targeted delivery of therapeutic and diagnostic agents. However, antibodies themselves have not been capable of reaching the cell nucleus in effective amounts. Most such antibodies react with the cell surface, and are gradually internalized, routed to lysosomes and degraded (Kyriakos et al., Cancer Res., 52:835 (1992)). Degregation products, including any radioisotopes attached thereto, then gradually leave the cell by crossing the lysosomal membrane and then the cell membrane. Although a conventional radioisotope label on an antibody degradation product can theoretically pass through the nuclear membrane and deliver some radioactivity to the nucleus (Woo et al., WO 90/03799) actual observations show that the amount is limited, and in any event, is insufficient to have a toxic effect on tumor cells.

Protein and polypeptide hormones and growth factors, particularly those having cell surface receptors, may be directly radiolabeled and used to target a tumor cell. As in the case of targeting radiolabeled antibodies, however, radioisotopes bound to amino acid residues of hormones, growth factors and the like exit from the cell after catabolism, and do not appreciably bind to nuclear material.

Despite the many advances in the field of cancer therapy and diagnosis, there remains an acute need for innovative treatment methods, particularly for cancers having high instances of relapse, which can be safely applied in a repetitive, long-term regimen, without the side effects produced by existing treatments.

SUMMARY OF THE INVENTION

The above-noted need is satisfied by the radiolabeled conjugates of the present invention which are capable of targeting and being selectively taken up and degraded by a tumor cell, and thereby delivering to the tumor cell nucleus a radioisotope capable of being incorporated into the nuclear material, so as to produce a cytotoxic effect and/or to render the cell detectable by radioimaging. The conjugates of the invention can be safely administered in long term cancer treatments, without producing significant adverse health effects.

In accordance with one aspect of the present invention, there is provided a cancer-specific radiolabeled conjugate of the formula:

(I)

wherein B* represents uracil substituted with a radionuclide; R represents H, OH, or O-L-DHT, L being a cleavable bifunctional linking moiety and DHT is 4-dihydrotestosterone, which is bound through its hydroxyl substituent to said linking moiety; and R' represents a phospho group or a substituted phospho group having the formula —PO(OR$_a$)(OR$_b$), —PO(OR$_a$)(ODHT) or —PO(ODHT)$_2$, R$_a$ and R$_b$ being the same or different and representing H or lower alkyl and DHT is as previously defined, with the proviso that at least one of the R and R' substituents comprises a DHT moiety.

The present invention also provides methods of using the above-described conjugate for treating and diagnosing cancers comprising cells having AR, especially ovarian, breast and prostate cancer.

The conjugates of the present invention have been designed so as to take advantage of two characteristics of many relapsing cancers, i.e. (1) relapsed/advance cancers have a large portion of rapidly growing and dividing cells (i.e. a large S-phase fraction); and (2) AR is expressed in practically all prostate cancer (primary and metastatic), ovarian cancer (>90% positive for AR regardless of the tumor site) and breast cancer (even when estrogen receptor (ER)-negative and progesterone receptor (PR)-negative, breast cancer cells express AR). Upon administration, the conjugate first binds to the sex hormone binding globulin, which in turn carries it exclusively to cells that have AR. Subsequent to this interaction, the entire conjugate is transported into the cell. Intracellular enzymes cleave the linking moiety, thus releasing and trapping within the cell the portion of the conjugate that is responsible for killing tumor cells. This cytotoxic effect is induced only when the cell cycle dependent therapeutic agent is incorporated into the DNA of dividing tumor cells. This dependence of radiotoxicity on the participation of the radiolabeled agent in DNA synthesis, in combination with relatively rapid pharmacokinetics, limits the exposure of normal tissue to radiation. In other words, the conjugate that remains in systemic circulation, or enters normal tissue or organs, is essentially innocuous. Accordingly, the radiolabeled conjugates of the invention may be administered frequently and without adverse effects.

BRIEF DESCRIPTION OF THE DRAWINGS

FIG. 1A plots the fraction of "bound" counts to "free counts" against "bound" $^{125}$IUdR-DHT (mM). FIG. 1B plots bound $^{125}$IUdR-DHT (mM) against free $^{125}$IUdR-DHT (mM).

FIG. 2A depicts the stability of $^{125}$IUdR-DHT with time in the presence or absence of OVCAR-3 cells. FIG. 2B depicts the kinetics of the emergence of $^{125}$IUdR in the medium in the presence or absence of OVCAR-3 cells.

DETAILED DESCRIPTION OF THE INVENTION

The conjugates of the present invention are composed of one component which is effective for killing cancer cells that make DNA and multiply and another component that is capable of specifically targeting AR expressed by cancer cells.

Thymidine analogs, such as IUdR, have certain characteristics which make their radiolabeled derivatives useful for the treatment or diagnosis of tumors whether macroscopically observable or not. Because such thymidine analogs are low-molecular-weight molecules, they diffuse readily within tissues. IUdR, for example, when radiolabeled with an Auger electron emitter, such as, $^{123}$I, $^{125}$I, $^{77}$Br, $^{80m}$Br, $^{195m}$Hg, and $^{113}$Sn, is innocuous outside the cell and ineffective at killing cells when within the cytoplasm. IUdR may also be radiolabeled with beta- or alpha-emitters such as, $^{131}$I, $^{32}$P, and radioisotopes of astatine (e.g., $^{225}$At). Unlike Auger electron emitters, these radioisotopes are radiotoxic even when outside of the cell. Such isotopes would allow for the irradiation of neighboring cells, i.e., a bystander effect, which is beneficial, particularly if AR expression is not uniform. IUdR is, for the most part, taken up selectively by dividing cancerous cells located within nondividing cells and is indefinitely retained following DNA incorporation. Nondividing cells will not incorporate radiolabeled IUdR into their DNA and most of the radiolabeled IUdR that is not taken up by cancerous cells will be catabolized/dehalogenated rapidly [$t_{1/2}$ of minutes] and thus will not incorporate into the DNA of distant noncancerous dividing cells. Furthermore, since it is a small molecule, radiolabeled IUdR will not induce an antibody response and as such lends itself to repeated injections, continuous infusion, or similar modes of administration.

In order to provide cancer cell specificity and enhanced delivery, the radiolabeled thymidine analogs are conjugated to an AR ligand. Radiolabeled IUdR, for example, is conjugated to the androgen ligand DHT. Importantly, AR is expressed on cells from a variety of cancers, such as 50–90% of breast tumors (Bryan, R. M., et al. (1984) Cancer, 54:2436–2440; Lea, O. A., et al. (1989) Cancer Res., 49:7162–7167; Soreide, J. A., et al. (1992) Eur. J. Surg. Oncol., 18:112–118). DHT, in addition to providing specific targeting of the conjugate to cells expressing AR, has also demonstrated anti-cancer effects in breast cancer experimental models (see, for example, Poulin, R., et al. (1988) Breast Cancer Res. Treat., 12:213–225) and other androgens, such as fluoxymesterone, have produced anti-cancer effects in administration to patients (see, for example, Ingle, J. N., et al. (1991) Cancer, 67:886–891).

Particularly preferred conjugates in accordance with the present invention have the formula wherein R and R' are as previously defined.

The term "lower alkyl", as used herein, refers to a straight or branched chain hydrocarbon group having 1 to 8 carbon atoms, preferably 1 to 4 carbon atoms.

Specific examples of conjugates within the scope of this invention are the following:

Synthetic routes for the preparation of these conjugates are exemplified hereinbelow.

In vitro studies conducted to date with certain of the specific conjugates described above have produced several notable results. First, coupling of DHT to $^{125}$IUdR produces cell killing agents which specifically target AR. Second, excess DHT competes with the DHT-containing conjugate for binding to AR. Third, uptake of the conjugate by the cell and metabolic processing of the conjugate is dependent on the presence of AR. Furthermore, in vivo studies have shown that certain of the above-described conjugates are bound specifically to the sex hormone binding globulin and are actively transported into cells that express AR and that uptake of $^{125}$IUdR transported to in vivo grown tumors in the form of conjugates with DHT is dependent on the AR-expression and results in the arrest of tumor growth.

Therapeutic preparations comprising the conjugates of this invention may be conveniently formulated for administration with a biologically acceptable vehicle, which may include the patient's own serum or serum fractions. Other suitable vehicles include liposomes and similar injectable suspensions, saline, activated carbon absorbents, and solutions containing cyclodextrins such as alphadex and betadex. Additionally, IUdR compounds may be derivatized, e.g. by esterification of available hydroxyl groups, with long chain fatty acids to increase the circulation half-life of the compounds. The concentration for diagnostic uses of the conjugate in the chosen vehicle should normally be from about 0.1 mCi/mL to about 10 mCi/mL. The concentration for therapeutic uses of the conjugate in the chosen vehicle should normally be from about 1 mCi/mL to about 100 mCi/mL. These concentrations may vary depending on whether the method of administration is intravenous, intraperitoneal, or intratumor. In all cases, any substance used in formulating a therapeutic preparation in accordance with this invention should be virus-free, pharmaceutically pure and substantially non-toxic.

If necessary, the action of contaminating micro organisms may be prevented by various anti-bacterial and/or anti-fungal agents, such as parabens, chlorbutinol, phenyl, sorbic acid, thimerosal and the like. It will often be preferable to include in the formulation isotonic agents, for example, glucose or sodium chloride. Additionally, free-radical scavengers and antioxidants such as ascorbic acid and the like may be employed to allow for a longer storage of the radioactive drug.

As used herein, the term "biologically acceptable vehicle" is intended to include any and all solvents, dispersion media and the like which may be appropriate for the desired route of administration of the conjugates described herein, either as such, or in the form of a pharmaceutical preparation, as described above. Except insofar as any conventional vehicle is incompatible with the conjugates of this invention, its use in formulating pharmaceutical preparations including such conjugates is contemplated. It is noted in this regard that administration of the conjugates of this invention with any substance that competes with the conjugate for AR binding is to be avoided.

The conjugates described herein may be administered parenterally to a patient, either as such or in combination with a biologically acceptable vehicle, as noted above, by conventional procedures. The preferred modes of administration are intravenous and intraperitoneal. For therapeutic applications, the conjugate will typically be administered at a dose that provides from about 1 mCi (37 MBq)-20 mCi (740 MBq) of radioactivity per 24 hours. The amount of the conjugate administered for diagnosis will generally be an amount sufficient to provide between 0.1 mCi and 10 mCi of radioactivity. For the registration of AR expression, the imaging can commence immediately after the administration. To detect DNA uptake, imaging may begin 1 hour after administration. Notably, with longer lived radioisotopes, imaging can occur at least daily for 7 days or longer to assess the tumor growth kinetics. The determination of an appropriate dose of the conjugate, either therapeutic or diagnostic, for a particular patient will, of course, be determined based on the type and stage of the patient's cancer and the judgment of the attending medical oncologist or radiologist, as the case may be.

As used herein, the term "patient" includes both humans and animals.

The targeted delivery of radio nuclides to cancer cells in the manner described herein produces strong cytotoxic activity, in that the radionuclide is introduced into the DNA of the multiplying cells, where it induces DNA strand breaks in the double helix. Moreover, by delivering radiolabeled agents to a specific site and relying on mechanisms operational at the site of delivery to release the radiolabeled agent, the usual in vivo degradation pathways are by-passed, bioavailability of the radiolabeled agent is improved and more tumor cells are exposed to the cell killing effect of the radiation as they enter into the S phase.

The following examples describe the synthesis of the aforementioned conjugates 1–5 of the present invention, as well as biological testing of certain of the conjugates. These examples are provided for illustrative purposes only and are not intended to limit the scope of the invention in anyway.

EXAMPLE I

Synthesis of $^{125}$IUdR-3'-succinyl-DHT Conjugate (Scheme 1)

A. Preparation of DHT Half Ester of Succinic Acid

Succinic acid anhydride (2 g, 20 mmol) and DHT (2 g, 6.9 mmol) were dissolved in anhydrous pyridine and 80 mg of 4-dimethylaminopyridine (DMAP) was added. The reaction flask was placed on a rotatory evaporator and approximately 20 mL of pyridine was evaporated under reduced pressure at 50° C. The reaction mixture was then stirred for 1 h at room temperature and ice-water was added (50 mL). The mixture was extracted with ethyl acetate (2×50 mL), washed with 5% citric acid, water and brine. The ethyl acetate layer was dried over anhydrous MgSO$_4$. The solvent was evaporated to dryness and an oily residue was treated with ethyl acetate/hexanes mixture to produce white precipitate of the crude DHT half-ester of succinic acid. The end product was collected by filtration and dried in vacuo. The purification of the DHT half-ester of succinic acid was accomplished on a silica gel column with dichloromethane/methanol mixture (10:0.4; v/v) as an eluant to give 2.12 g (78% yield) of the pure half ester.

B. Preparation of 5'-Dimethoxytrityl-$^{125}$IUdR

Dimethoxytrityl chloride (4 g, 11.3 mmol) is added in two portions into a stirred solution of 5-iodo-2'-deoxyuridine (4 g, 11.4 mmol; IUdR) in 50 mL anhydrous pyridine at room temperature. The mixture is stirred overnight. Pyridine is evaporated to dryness and an oily residue is dissolved in 100 mL ethyl acetate, washed with water, 10% citric acid, aqueous saturated sodium bicarbonate solution, and saline. The washed organic layer is dried over MgSO$_4$. Ethyl acetate is evaporated to dryness giving a crude DMT-IUdR in the from of a glass-like residue, which is redissolved in ethyl acetate/ethyl ether mixture, filtered and allowed to crystallize at 4° C. overnight. The crystalline, pure DMT-IUdR is collected by filtration. The volume of the filtrate is reduced under vacuum and a silica gel column is used to purify the remaining DMT-IUdR using dichloromethane/methanol (10:0.5; v/v) as a column solvent.

C. Conjugation Reaction and Deprotection

As shown in Scheme 1 below, purified DMT-IUdR (4 g, 6.01 mmol) is dissolved in 3 mL freshly distilled from CaH$_2$ anhydrous dichloromethane and the DHT half-ester of succinic acid, prepared a previously described, (2.35 g, 6.0 mmol) is added. To this mixture dicyclohexylcarbodiimide (1.26 g, 6.2 mmol; DCC) is added in the presence of 80 mg of 4-dimethylaminopyridine (DMAP). The mixture was stirred at room temperature and the reaction progress was monitored on TLC. When the esterification was complete, the reaction mixture was diluted with ethyl ether (10 mL) and filtered to remove dicyclohexylurea (DCU). The filtrate was washed with water, citric acid and brine and was dried over MgSO$_4$. The residue of crude 5'-DMT-protected 6 obtained after evaporation of the solvent was purified on a silica gel column using ethyl acetate/hexanes (3:2; v/v) as a solvent. The yield of 5'-DMT-protected 6 was 3.1 g (50%). The 5'-DMT-protected 6 (3 g) was dissolved in 25 mL of 2-propanol and 1 mL of 90% CF$_3$COOH (TFA) was added. After approximately 4 hours at room temperature, TLC indicated that 100% of the DMT protection was removed to generate 5'-deprotected derivative 6. After evaporation of the solvent, the residue was treated with 5 mL water and evaporated again to remove the majority of TFA. The glassy residue was dissolved in dichloromethane and dried over MgSO$_4$. The crude product was purified on a silica gel column with ethyl acetate/hexanes (15:10; v/v) as a solvent to give 2.8 g (82%) of pure conjugate 6. The deprotection of 5'-DMT derivative 6 with trifluoroacetic acid can also be conducted in tert-butanol as a solvent.

D. Preparation of Stannyl Derivatives and Radiolabeling Procedure

The preparation of the 5-trialkylstannyl-derivatives (7) is accomplished as described in U.S. Pat. No. 5,468,853 to Baranowska-Kortylewicz which is commonly owned with its present application. The radiolabeling is also accomplished using procedures described in U.S. Pat. No. 5,468,853. The radioisotopes that can be utilized in this protocol include radiohalides such as radioiodine, radiobromine, and radioastatine. The reaction can be conducted with radiochlorine, but not as efficiently, and it does not work for radiofluorine. Suitable oxidants include: iodogen, chloromine-T, N-chlorosuccinimide, hydrogen peroxide, tert-butyl hydroperoxide (T-HYDRO solution; 70% wt in water) and cerium ammonium nitrite.

because the half-life is short, repeated injections should be possible without a large radioactive burden in normal tissue.

EXAMPLE II

Synthesis of 5'-monophosphate-$^{125}$IUdR-3'-succinyl-DHT Conjugate (Schemes 2 and 3)

A. Phosphorylation Reaction

IUdR (1.5 g, 4.25 mmol) was dissolved in 7 mL of DMF/THF mixture (3:4; v/v) under strictly anhydrous con- Scheme 1

The conjugate obtained by this synthesis is relatively hydrophobic but still soluble in aqueous media at "no-carrier-added" radioactivity levels. The release of $^{125}$IUdR from the succinate ester appears to be very effective, both in vitro in cell culture and in vivo in tumor bearing animals. The half-life in vivo is short and may be detrimental to the delivery of therapeutic doses to tumor. On the other hand, ditions. After cooling to 0° C., 1H-tetrazole (1.2 g, 17.1 mmol) and di-tert-butyl diisopropylphosphoramidite (1.65 mL, 5.1 mmol) were added. The mixture was stirred at 0–4° C. for 72 h. Tert-Butyl hydroperoxide (4.6 mL) was added at −80° C. and the mixture was allowed to slowly warm up to room temperature. A 5% solution of NaHSO$_3$ (10 mL) was added and the whole mixture was evaporated to dryness.

The residue was extracted with dichloromethane (2×50 mL) and the organic layer dried with MgSO$_4$. A mixture of all possible phosphorylated derivatives of IUdR was obtained, i.e., 3'-monosubstituted, 5'-monosubstituted and 3',5'-disubstituted. Separation of the desired 5'-isomer was accomplished on a silica gel column with chloroform/methanol (10:0.6; v/v) as a solvent. The desired pure 5'-monosubstituted derivative (8) was isolated in 52% yield. The final purification was accomplished by crystallization from ethyl ether to give white solid, mp. 121–123° C.

B. Conjugation Reaction and Radiolabeling

The DHT half-ester of succinic acid, prepared as described in Example 1 above, (0.77 g, 1.46 mmol) was dissolved in 10 mL of anhydrous dichloromethane. Dicyclohexylcarbodiimide (DCC; 0.32 g, 1.5 mmol) was added followed by phosphorylated IUdR (8) (0.8 g, 1.46 mmol) and DMAP (70 mg). The reaction mixture was stirred at room temperature until starting materials disappeared as determined by TLC. The solvent was evaporated under vacuum and replaced with ethyl acetate/hexanes mixture (3:2; v/v). The precipitated DCU was removed by filtration and the filtrate was washed with citric acid and water. The organic layer was dried under MgSO$_4$ and evaporated again. The purification of the resulting conjugate 9 was done on a silica gel column using chloroform/methanol mixture (10:0.6; v/v) as a solvent. The final pure conjugate was obtained in 49% yield (0.66 g).

The stannyl derivative was prepared and radiolabeling was carried out in the same general manner as in Example 1, above. Removal of the protecting t-butyl group was effected by a breif exposure of the 125I-labeled derivative to the HPLC solvent which is typically 0.05% to 0.5% trichloroacetic acid (TCA) in acetonitrile at room temperature.

Scheme 2

An alternative approach to the synthesis of conjugate 2 is shown in Scheme 3, in which the conjugation reaction is carried out prior to phosphorylation. However, Scheme 2 has been found to produce the desired conjugate in higher yield.

Scheme 3

Conjugate 2 is the most hydrophilic of the conjugates described herein (two negative charges on the monophosphate group). It cannot cross the cell membrane by itself, i.e., it requires the active transport mechanism from the systemic circulation into the tumor cells with the aid of sex hormone binding globulin.

EXAMPLE III

Synthesis of 5'-[$^{125}$I]iodo-2'-deoxy-5'-monophosphate-O-methyl-O-(mono-dihydrotestosterone) (Scheme 4)

A. Preparation of N,N-diisopropylmethylphoshoramidate of DHT

Dihydrotestosterone (5α-androstan-17β-ol-3'-one; 2 g, 6.9 mmol) was dissolved in 30 mL of anhydrous THF under nitrogen. N,N-Diisopropylethylamine (DEPA; 1.78 g, 13.8 mmol) and DMAP (20 mg, 0.13 mmol) were added. A stirred mixture was cooled to 0° C. and N,N-diisopropylmethylphosphoamidic chloride (2.05 g, 10.33 mmol) was added neat in five 0.5-mL portions. Stirring was continued at 0° C. for 30 min. The precipitate was filtered off and the filtrate was evaporated to dryness under vacuum. A crude product was purified on a silica gel column using dichloromethane/ethyl acetate/triethylamine (10/10/0.05; v/v) as a solvent. Only partial purification was achieved and the material obtained from the column was used in the following step of the synthesis.

B. Preparation of 5-Iodo-2'Deoxyuridine-5'-Monomethylphosphate-3'-Succinyl DHT

A solution of the freshly prepared N,N-diisopropylmethylphosphoramidate of DHT (1.55 g, 3.4 mmol) in anhydrous THF (20 mL) was cooled to 0° C. and 1H-tetrazole (1.4 g, 20 mmol) was added followed by IUdR (1.1 g, 3.1 mmol) dissolved in 5 mL anhydrous DMF. The mixture was allowed to react overnight at 0°–2° C. Tert-Butyl hydroperoxide (4 mL, 70% w solution in water) was added at −10°

C. The mixture was allowed to slowly reach room temperature and after 1 hour of stirring at room temperature the solvent was evaporated to dryness under vacuum. The semi-solid residue was extracted with dichloromethane (2×50 mL) and washed with 5% NaHSO$_3$ and water. During the extraction unreacted IUdR was separated and removed by filtration. The filtrate was dried over MgSO$_4$ and again evaporated to dryness. The residue was analyzed on TLC plate and revealed the presence of two UV-positive spots along with a small residual spot corresponding to unreacted IUdR. The two UV-positive components were separated on a silica gel column using dichloromethane/methanol mixture (10:0.6; v/v) as a solvent. The major component (TLC R$_f$=0.65) was identified as a 5'-regioisomer (12) and was obtained after the column chromatography in 63% yield (1.23 g).

The stannyl derivative (14) was prepared and radiolabeling was carried out in the same general manner as in Example 1, above.

Conjugates 4 and 4A possess interesting characterisitics in that the negative charge on the monophosphate—either already present as in conjugate 3 or generated after administration by circulating carboxylases—will prevent the uptake of this drug via passive diffusion (charged molecules cannot readily cross the cell membrane, they require the active transport mechanism to be able to enter cancer cells), thus improving the selectivity. This is very similar to conjugate 2, but the DHT on phosphate is more stable compared to succinate esters.

EXAMPLE IV

Synthesis of 5'-[$^{125}$I]iodo-2'-deoxy-5'-monphosphate-O-(bis-dihydrotestosterone) (Scheme 5)

A. Preparation of N,N-diisopropylphosphoramidite (DHT)$_2$

Diisopropylphosphoramidous dichloride (0.65 mL, 3.45 mmol) was added to a stirred solution of DHT (2 g, 6.9

Alternatively, the method of scheme 4 can be performed using the N,N-diisopropylmethylphosphoramidate of DHT, and following the same procedure described above except that the methyl group is hydrolyzed prior to the stannylation reaction. The final reaction product of scheme 4 with this modification is 5'-[$^{125}$I]iodo-2'-deoxy-5'-monophosphate-O-(mono-dihydrotestosterone) (4A).

mmol) containing 1.5 mL (8.5 mmol) of DEPA and 65 mg of DMAP in 50 mL anhydrous THF at 0° C. Copious amounts of white precipitate were formed. The stirring was continued for 2 hours at room temperature. The precipitate was removed by filtration and the filtrate was evaporated to dryness. The crude product was partially purified on a silica gel column using dichloromethane/ethyl acetate/triethylamine (10/5/0.05; v/v) as a solvent. The partially purified (approximately 95% pure) N,N-diisopropylphophoramidite $(DHT)_2$ was used in the following reaction.

B. Preparation of 5-Iodo-2'Deoxyuridine-5'-Mono-O-(bis-dihydrotestosterone)phosphate A solution of freshly prepared N,N-diisopropylphosphoramidite of DHT (2.1 g, 2.92 mmol) in 20 mL of anhydrous THF was stirred at 0° C. while 1H-tetrazole (1 g, 14.2 mmol) followed by IUdR (2 g, 5.65 mmol) as a solution in 5 mL of anhydrous DMF were added sequentially. This reaction mixture was stirred at 0°–2° C. overnight. After cooling to −10° C., 4 mL of tert-butyl hydroperoxide was added and with constant stirring. The mixture was allowed to reach room temperature over a period of 30 min. The white precipitate was filtered off and the filtrate was treated with 5% $NaHSO_3$ (10 mL). The organic layer was evaporated to dryness and the residue was kept under high vacuum for 1 hour. The residue was extracted with dichloromethane (2×50 mL) and the combined extracts were washed with water, $NaHCO_3$ and dried over $MgSO_4$. The solvent was evaporated to dryness and the residue containing two UV-positive components ($R_f$ 0.58 and $R_f$ 0.40 on TLC) were separated and purified on a silica gel column using dichloromethane/methanol (10:0.7; v/v) as a solvent to give 0.9 g ($R_f$ 0.58) and 0.15 g ($R_f$ 0.40) of the two regioisomers. The faster isomer ($R_f$ 0.58) was identified as pure conjugate 13.

The stannyl derivative 15 was prepared and radiolabeling was carried out in the same general manner as in Example 1, above.

Conjugate 5 is the most hydrophobic of all the conjugates described herein. It may be best suited for local/regional administration (e.g., intraperitoneal in the case of ovarian cancer) with a slow diffusion from the site of injection.

EXAMPLE V

Binding of $^{125}$IUdR-DHT to OVCAR-3 Cells In Vitro

To generate a Scatchard plot for the binding of $^{125}$IUdR-DHT to OVCAR-3 cells, OVCAR-3 cells were thawed from a stock or freshly harvested by a lavage of the peritoneal cavity of athymic mice bearing intraperitoneal ascites OVCAR-3 tumors. The cells were twice washed with full media (RPMI 1640 medium with 2 mM L-glutamine adjusted to contain 1.5 g/L sodium bicarbonate, 4.5 g/L glucose, 10 mM HEPES, and 1.0 mM sodium pyruvate and supplemented with 0.01 mg/ml bovine insulin, 80%; fetal bovine serum, 20%). The cells were spun at 450 rpm for 10 minutes to collect a cell pellet and were then resuspended in full media to achieve approximately $5 \times 10^6$ cells/mL. The cells were counted and their viability was determined by Trypan Blue staining. "Cold" dihydrotestosterone (DHT) was dissolved in 95% ethanol to create a stock solution of 5 µg/mL. Similarly, 95% ethanol was added to $^{125}$IUdR-DHT to produce 250,000 cpm/100 µL. Forty samples were prepared in plastic tubes as set forth in Table 1.

TABLE 1

| Tube number | cells | $^{125}$IUdR-DHT cpm (µL) | "cold" DHT ug (µL) | 95% EtOH µL |
|---|---|---|---|---|
| 1 a, b | $5 \times 10^6$ | 250,000 (100) | 5 (10) | 0 |
| 2 a, b | $5 \times 10^6$ | 200,000 (80) | 5 (10) | 20 |
| 3 a, b | $5 \times 10^6$ | 150,000 (60) | 5 (10) | 40 |
| 4 a, b | $5 \times 10^6$ | 125,000 (50) | 5 (10) | 50 |
| 5 a, b | $5 \times 10^6$ | 100,000 (40) | 5 (10) | 60 |
| 6 a, b | $5 \times 10^6$ | 75,000 (30) | 5 (10) | 70 |
| 7 a, b | $5 \times 10^6$ | 50,000 (20) | 5 (10) | 80 |
| 8 a, b | $5 \times 10^6$ | 25,000 (10) | 5 (10) | 90 |
| 9 a, b | $5 \times 10^6$ | 12,500 (5) | 5 (10) | 95 |
| 10 a, b | $5 \times 10^6$ | 0 (0) | 5 (10) | 100 |
| 11 a, b | $5 \times 10^6$ | 250,000 (100) | 0 | 10 |
| 12 a, b | $5 \times 10^6$ | 200,000 (80) | 0 | 30 |
| 13 a, b | $5 \times 10^6$ | 150,000 (60) | 0 | 50 |
| 14 a, b | $5 \times 10^6$ | 125,000 (50) | 0 | 60 |
| 15 a, b | $5 \times 10^6$ | 100,000 (40) | 0 | 70 |
| 16 a, b | $5 \times 10^6$ | 75,000 (30) | 0 | 80 |
| 17 a, b | $5 \times 10^6$ | 50,000 (20) | 0 | 90 |
| 18 a, b | $5 \times 10^6$ | 25,000 (10) | 0 | 100 |
| 19 a, b | $5 \times 10^6$ | 12,500 (5) | 0 | 105 |
| 20 a, b | $5 \times 10^6$ | 0 (0) | 0 | 110 |

Figure 1:
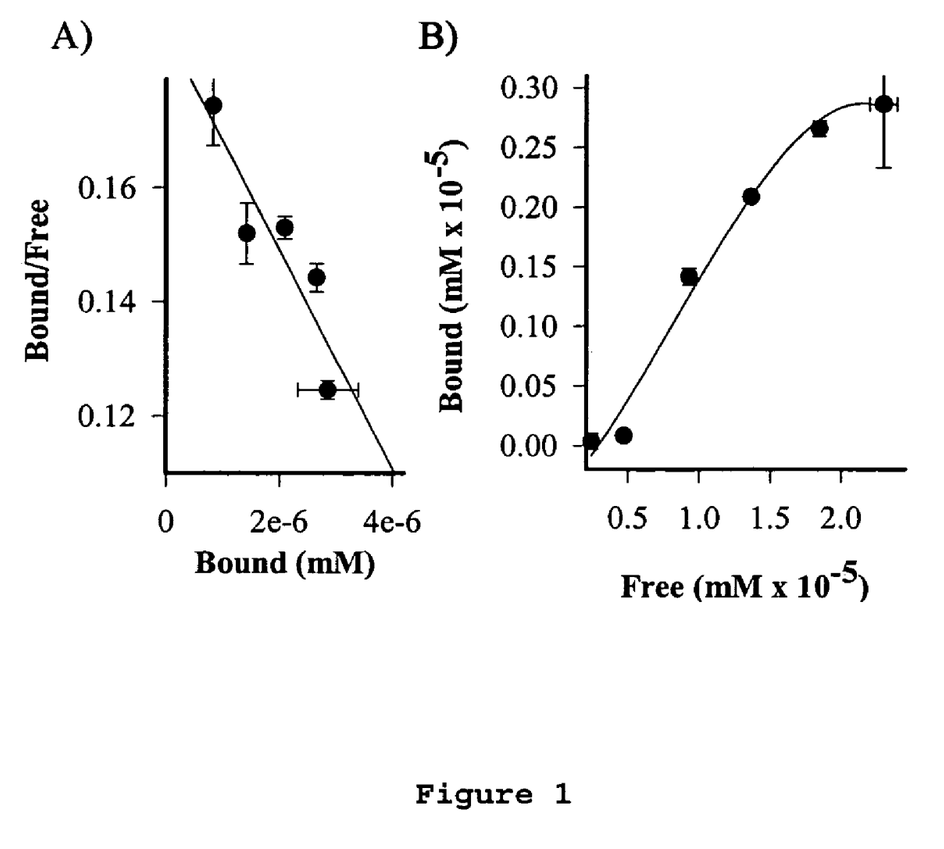
FIG. 1 is a set of two graphs depicting the binding of $^{125}$IUdR-DHT to OVCAR-3 cells in vitro.

The tubes were capped and gently vortexed. The "total applied" counts were then determined in a gamma counter. The samples were then incubated at 0–4° C. with shaking for 14–16 hours. The cells were centrifuged at 1,000 rpm for 15 minutes at 4° C. to generate a cell pellet. A known volume of the supernatant from the centrifugation was transfered to new plastic tubes and counted in a gamma counter to determine the "free" counts. The cell pellet with the remainder of the supernatant was then counted in the gamma counter. "Bound" counts were then determined by subtracting counts associated with the supernatant from the remaining counts. Plots of this data can be found in FIG. 1. The data show a single type of binding sites with a high affinity for $^{125}$IUdR-DHT. Use of the excess DHT revealed that the high affinity seen is due to the DHT portion of the drug and thus dictated by the presence of AR.

To determine the strength of the interaction of $^{125}$IUdR-DHT with the cells, the cells were then washed with ice-cold phosphate buffered saline (PBS) and gently centrifuged. Again, a known volume of the supernatant was removed and both the supernatant and pellet were counted in the gamma counter.

For general binding assays, OVCAR-3 cells were harvested by a lavage of the peritoneal cavity of athymic mice bearing intraperitoneal ascites OVCAR-3 tumors. Cells were washed with Hank's balanced salt solution (HBBS), resuspended in RPMI 1640 medium without serum and used in a binding assay.

Alternatively, cells harvested from the intraperitoneal ascites tumors were plated in tissue culture flasks (T25) at $1 \times 10^6$ cells/mL in RPMI 1640 with added penicillin, streptomycin, L-glutamine and 10% fetal bovine serum. The cells were allowed to reach about 70% confluency and the serum-containing medium was aspirated and replaced with serum-free medium (SFM). The cells were allowed to remain in SFM for 24 hours. After 24 hours, the medium was aspirated and SFM containing 10 nM dihydrotestosterone (DHT) was added to three flasks. The volume of added SFM was carefully measured to assure that each flask received an identical volume of SFM. To the another three flasks an identical volume of SFM without DHT was added. The cells were incubated overnight. The medium was removed from all flasks and the cells were washed with 40 mM HEPES supplemented with 0.1% bovine serum albumin (0.1 g BSA in 100 mL HEPES), pH 7.4. $^{125}$IUdR-DHT derivative was dissolved in HEPES/BSA buffer to produce a final concentration of about 50,000 cpm/mL. An identical volume of $^{125}$I-DHT-containing buffer was added to all six flasks and incubated for 5 hours at 4° C. The medium was aspirated and 1 mL aliquots were counted in a gamma counter to determine cpm/mL after incubation. Cells were washed two times with ice-cold PBS containing 0.1% BSA. The washes were combined, the total volume measured, and 1 mL aliquots were counted in a gamma-counter. To the cells, 5 mL of 1 M NaOH was added and incubated for two hours. The NaOH wash was collected and 1-mL aliquots were counted in a gamma-counter. One mL PBS was added to the remaining cells and the cells were scraped and transferred into gamma-counter tubes to determine cpm/mL. This procedure may be employed to determine competitive binding wherein the amount of cpm in the NaOH-treated cell pellet in the absence of "cold" DHT is the "total bound" and the amount of cpm in NaOH-treated cells that were incubated with "cold" DHT can yield the amount of nonspecific binding. This method works well with cells that grow as monolayers such as PC3, LNCaP, and DU-145 cells.

EXAMPLE VI

Stability of $^{125}$IUdR

Figure 2:
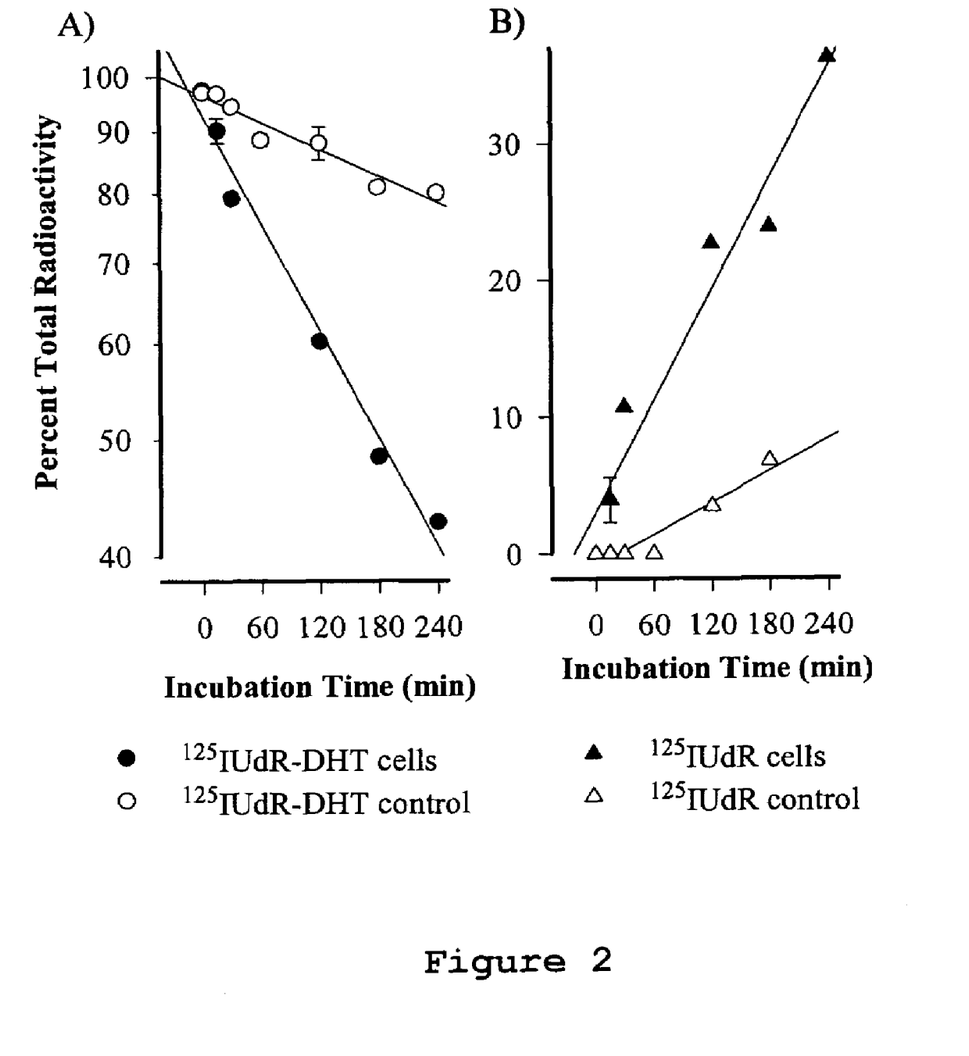
FIG. 2 is a set of two graphs depicting the stability of $^{125}$IUdR-DHT.

OVCAR-3 cells in full growth medium (RPMI 1640 medium with 2 mM L-glutamine adjusted to contain 1.5 g/L sodium bicarbonate, 4.5 g/L glucose, 10 mM HEPES, and 1.0 mM sodium pyruvate and supplemented with 0.01 mg/ml bovine insulin, 80%; fetal bovine serum, 20%) at $1 \times 10^6$ cells per flask were plated onto three Petri dishes and allowed to attach for 24 hours. As a control, one dish without cells was subjected to the same treatments. After 24 hours, the cells were trypsinized from one dish to determine cell number and viability. The media was then aspirated from the remaining dishes, including the control, and replaced with 1 mL of fresh media. 0.1 mCi of $^{125}$IUdR-DHT in 0.10 mL of ethanol was added to all of the dishes. The dishes were incubated at 37° C. At 0, 5, 15, 30, 60, 120, 180, and 240 minutes, 10 µL of media was removed from each of the dishes of which 2 µL was added to a silica gel TLC plate. Additionally, 2 µL was added to glass gamma counter tubes as standards. The TLC plates were run with a 3:1 mixture of ethyl acetate and hexane (v/v). When the solvent front approached the end of the plate, the plate was removed from the solvent, dried, and cut into strips. The standards and the strips were then counted. The percent recovered $^{125}$IUdR-DHT was calculated as a ratio of the intact $^{125}$IUdR-DHT at a given timepoint divided by the intact $^{125}$IUdR-DHT at the 0 minute timepoint (see FIG. 2A). Similar calculations were used to determine the kinetics of the appearance of $^{125}$IUdR in the medium, which was determined to occur at a rate of 8.5%/hour (FIG. 2B). This rate is in comparison to the disappearance of $^{125}$IUdR-DHT from the media at a rate of 16%/hour. Notably, $^{125}$IUdR is freely diffusible from cells and therefore only a fraction of $^{125}$IUdR-DHT hydrolyzed in cells is used for DNA synthesis. The inclusion of a negatively-charged monophosphate assists in the retention of these compounds in the cell.

EXAMPLE VII

Binding of 5'-MP-$^{125}$IUdR-DHT to Sex Hormone Binding Globulin

Typically, the testosterone or DHT signaling in AR-positive cells involves sex hormone binding globulin (SHBG). Human SHBG-DHT complexes interact with plasma membranes of several sex steroid-dependent cells and tissues. This interaction involves the binding of SHBG to a specific membrane protein receptor, which promotes its cellular internalization. The next step entails binding to AR and conformational changes in AR. AR is subsequently translocated to the nucleus where it dimerizes and binds DNA. The overall process allows for the intracellular delivery of the $^{125}$IUdR drugs only to cells expressing AR.

To assay the binding of 5'-MP-$^{125}$IUdR-3'-DHT to SHBG, a 0.1 mg/mL solution of SHBG in 0.1 M Tris buffer, pH 7.6 containing 0.1% bovine serum albumin was prepared as a stock solution. Additionally, a solution of 0.1 mCi/mL 5'-MP-$^{125}$IUdR-3'-DHT in 50% ethanol and a solution of 0.05 mg/mL DHT in 50% ethanol were prepared. Twenty samples of were prepared as set forth in Table 2 with the 5'-MP-$^{125}$IUdR-3'-DHT being added last.

TABLE 2

| tube | SHBG mL | DHT mL | 5'-MP-$^{125}$IUdR-3'-DHT (mL) | Tris buff mL | 50% EtOH mL |
|---|---|---|---|---|---|
| 1 | 0.2 | 0.000 | 0.01 | 0.590 | 0 |
| 2 | 0.2 | 0.000 | 0.01 | 0.590 | 0 |
| 3 | 0.2 | 0.002 | 0.01 | 0.588 | 0 |
| 4 | 0.2 | 0.002 | 0.01 | 0.588 | 0 |
| 5 | 0.2 | 0.004 | 0.01 | 0.586 | 0 |
| 6 | 0.2 | 0.004 | 0.01 | 0.586 | 0 |
| 7 | 0.2 | 0.008 | 0.01 | 0.582 | 0 |
| 8 | 0.2 | 0.008 | 0.01 | 0.582 | 0 |
| 9 | 0.2 | 0.016 | 0.01 | 0.574 | 0 |
| 10 | 0.2 | 0.016 | 0.01 | 0.574 | 0 |
| 11 | 0.2 | 0.032 | 0.01 | 0.558 | 0 |
| 12 | 0.2 | 0.032 | 0.01 | 0.558 | 0 |
| 13 | 0.2 | 0.064 | 0.01 | 0.526 | 0 |
| 14 | 0.2 | 0.064 | 0.01 | 0.526 | 0 |
| 15 | 0.2 | 0 | 0.01 | 0.526 | 0.064 |
| 16 | 0.2 | 0 | 0.01 | 0.526 | 0.064 |
| 17 | 0.2 | 0 | 0.01 | 0.574 | 0.016 |
| 18 | 0.2 | 0 | 0.01 | 0.574 | 0.016 |
| 19 | 0.2 | 0 | 0.01 | 0.586 | 0.004 |
| 20 | 0.2 | 0 | 0.01 | 0.586 | 0.004 |

Figure 3:
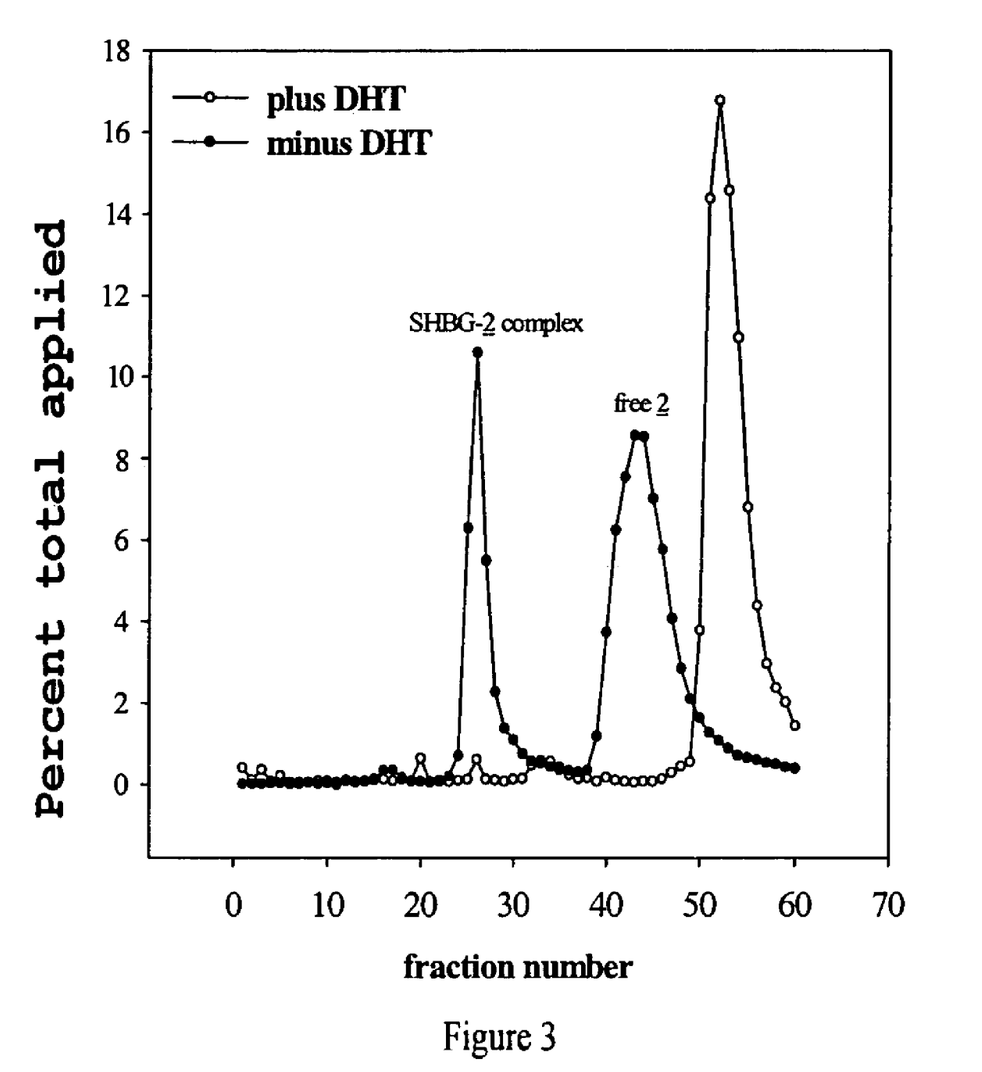
FIG. 3 is a graph showing the HPLC profiles of 5'-MP-$^{125}$IUdR-3'-DHT with SHBG in the presence or absence of DHT.

The tubes were then vortexed for about 30 seconds and incubated for 10 minutes in a water bath at 37° C. The samples were then incubated at 0–4° C. for 3 hours. 0.1 mL aliquots were removed from the samples and counted in a gamma counter. To each tube, 0.4 mL of ice-cold charcoal-dextran solution was added and the tubes were incubated on ice for 15 minutes. The samples were then centrifuged at 4° C. for 20 minutes at 1,000 rpm. 0.5 ml aliquots were taken for gamma-counting and the residue was also counted. Selected samples were analyzed by size-exclusion HPLC (tandem TSK2000 and TSK3000 size exclusion columns (TosoHaas; Montgomeryville, Pa.) with a guard column using PBS, pH7.2 as the eluant). As seen in FIG. 3, SHBG specifically bound 5'-MP-$^{125}$IUdR-3'-DHT and this interaction was competed away with "cold" DHT.

EXAMPLE VIII

In Vivo Effects of 5'-MP-$^{125}$IUdR-3'-DHT

Figure 4:
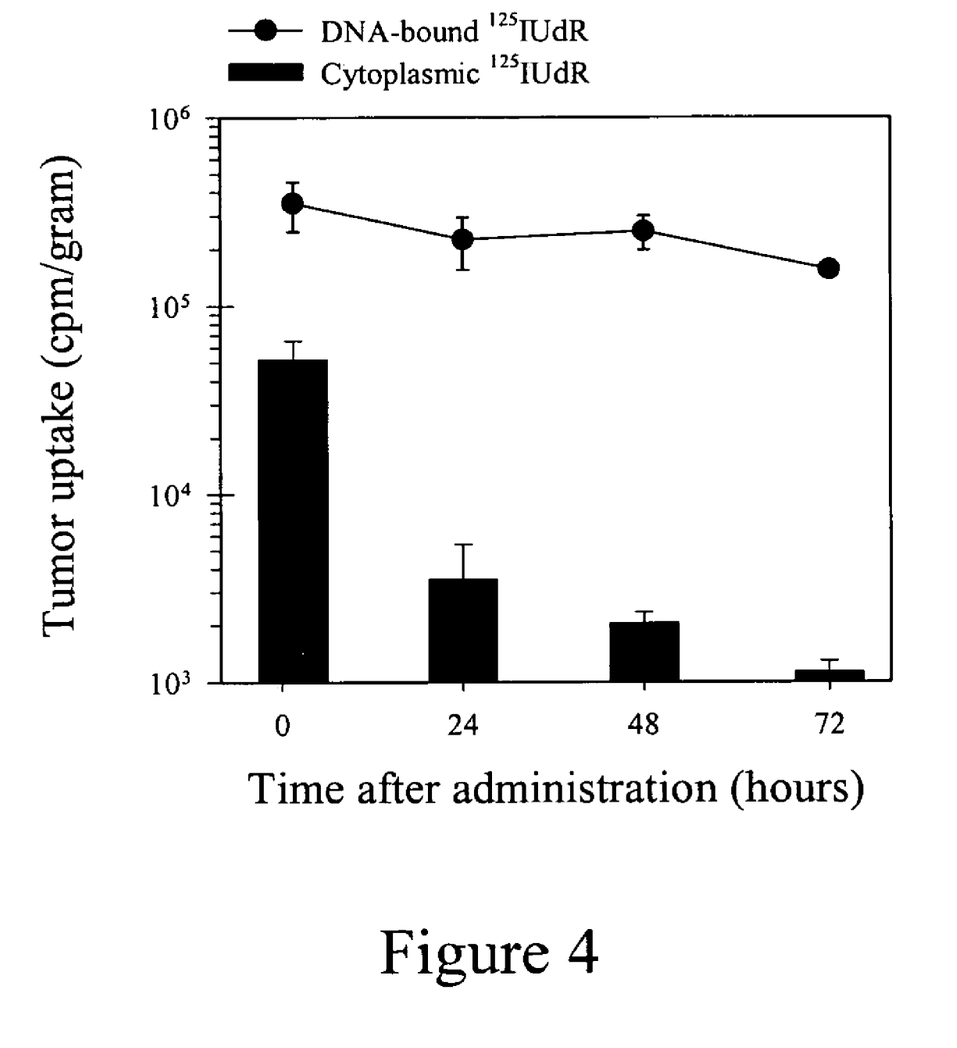
FIG. 4 is a graph sowing the tumor uptake of 5'-MP-$^{125}$IUdR-3'-DHT in athymic mice (bars) and the amount of DNA-bound $^{125}$IUdR (line).

Athymic mice bearing intraperitoneal OVCAR-3 tumors were treated with 0.05 mCi (1.4 kBq) 5'-MP-$^{125}$IUdR-3'-DHT intraperitoneally. Tumor cells were recovered by peritoneal lavage from the mice at 0, 24, 48, and 72 hours after 5'-MP-$^{125}$IUdR-3'-DHT administration. The cells were washed with phosphate buffered saline. The cells were subsequently pelleted and counted in a gamma counter to determine tumor uptake (n=5; FIG. 4). To determine the amount of DNA-bound $^{125}$IUdR, the cells were fractionated using a Wako kit (Wako Cemicals USA, Inc., Richmond, Va.) or, alternatively, with a NE-PREP nuclear and cyoplasmic extraction kit (Pierce, Rockford, Ill.) per the manufacturer's instruction. The distribution of radioactivity in the cytoplasm and DNA were measured and normalized to tumor size (FIG. 4).

Figure 5:
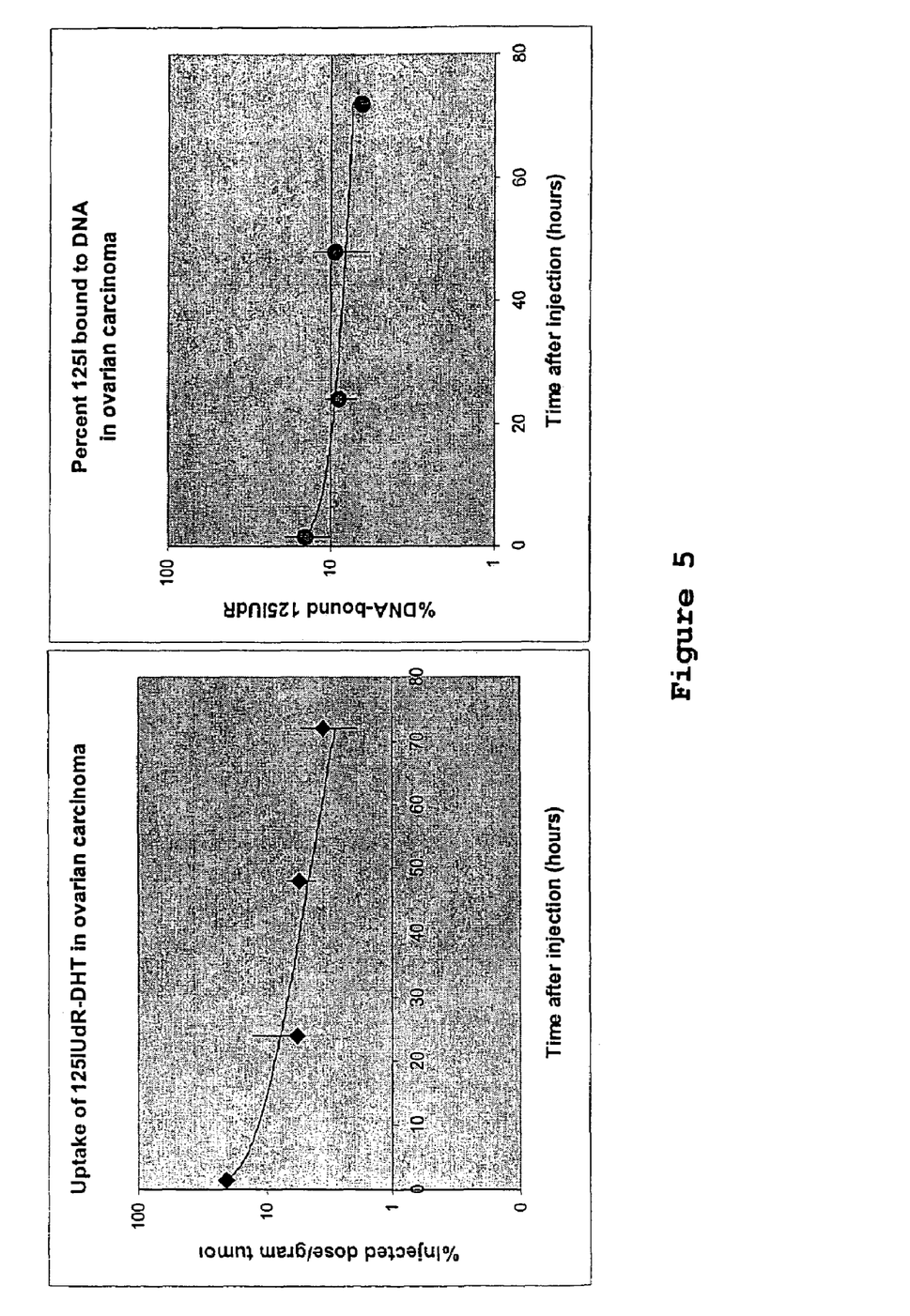
FIG. 5 is a set of two graphs showing the in vivo uptake of $^{125}$IUdR-3'-DHT by OVCAR-3 tumors in athymic mice (A) and the amount bound to DNA (B) over time.

With regard to $^{125}$IUdR-3'-DHT, the biodistribution of the reagent (0.001–0.010 mCi/mouse; 0.027–0.27 kBq/mouse) in athymic mice bearing AR-expressing OVCAR-3 tumors is seen in Table 3. Additionally, the efficacy of the reagent against the intraperitoneal OVCAR-3 tumors after 6 fractionated doses (0.1 mCi/dose/mouse; 2.7 kBq/dose/mouse) is seen in Table 4. The tumor uptake of $^{125}$IUdR-3'-DHT and the incorporation into DNA over time is shown in FIG. 5.

TABLE 3

| | Percent injected dose per gram tissue average of n = 10 (standard deviation) | | | |
|---|---|---|---|---|
| | 1.5 h | 24 h | 48 h | 72 h |
| Blood | 29.61 | 0.25 | 0.30 | 0.17 |
| | (5.22) | (0.08) | (0.15) | (0.00) |
| OVCAR-3 tumor (IP) | 20.70 | 5.66 | 5.41 | 3.54 |
| | (0.95) | (0.37) | (0.73) | (0.27) |
| solid OVCAR-3* | 12.94 | 0.67 | 0.28 | 0.24 |
| | (1.56) | (0.46) | (0.01) | (0.01) |
| Brain | 1.91 | 0.03 | 0.05 | 0.04 |
| | (0.39) | (0.01) | (0.01) | (0.00) |
| Kidney | 17.67 | 0.20 | 0.18 | 0.22 |
| | (3.18) | (0.02) | (0.01) | (0.01) |
| Spleen | 15.60 | 0.59 | 0.44 | 0.59 |
| | (2.82) | (0.02) | (0.04) | (0.11) |
| Liver | 11.07 | 0.24 | 0.32 | 0.33 |
| | (2.92) | (0.04) | (0.06) | (0.03) |
| Uterus | 11.43 | 0.54 | 0.66 | 0.97 |
| | (0.42) | (0.21) | (0.33) | (0.34) |

*on average approximately 2 mice in each group developed solid IP tumors

TABLE 4

| | $^{125}$IUdR-DHT | $^{125}$IUdR-DHT with excess "cold" DHT to block uptake of the radioactive drug | Shamtreatment (control mice) |
|---|---|---|---|
| mean tumor burden (g) | 0.304 ± 0.320* | 0.635 ± 0.332 | 1.955 ± 1.109 |
| median tumor size (g) | 0.244 | 0.533 | 1.864 |

TABLE 4-continued

|  | $^{125}$IUdR-DHT | $^{125}$IUdR-DHT with excess "cold" DHT to block uptake of the radioactive drug | Shamtreatment (control mice) |
| --- | --- | --- | --- |
| range (g) | 0.012–0.781 | 0.192–1.238 | 0.515–3.402 |
| tumor growth reduction | −670% | −230% | 0% |

*average (n = 10) and standard deviation

Notably, the stability of $^{125}$IUdR-3'DHT in the presence of OVCAR-3 cells showed that the emergence of "free" $^{125}$IUdR in the growth medium requires interaction of the drugs with specific cells. This experiment also showed that the first step in the enzymatic hydrolysis of the reagent appears to be the removal of the DHT moiety. This allows at least a partial retention of the negatively charged succinate inside the cell where the next hydrolytic step frees $^{125}$IUdR to be taken up by DNA.

A number of literature and patent references are cited in the foregoing specification in order to more fully describe the state of the art to which this invention pertains. The entire disclosure of each of these citations is incorporated by reference herein.

While certain embodiments of the present invention have been described and/or specifically exemplified above, various other embodiments will be apparent to those skilled in the art from the foregoing disclosure. The present invention is, therefore, not limited to such embodiments, but is capable of considerable variation and modification without departing from the scope of the following claims.

What is claimed is:

1. A cancer-specific radiolabeled conjugate of the formula:

(I)

wherein B* represents uracil substituted with a radionuclide; R represents H, OH, or O-L-DHT, L being a cleavable bifunctional linking moiety and DHT is 4-dihydrotestosterone which is bound through its hydroxyl substituent to said linking moiety; and R' represents H or a group having the formula —PO(OR$_a$)(OR$_b$), —PO(OR$_a$)(ODHT) or —PO(ODHT)$_2$, R$_a$ and R$_b$ being the same or different and representing H or lower alkyl having 1–8 carbon atoms and DHT is as previously defined, with the proviso that at least one of the R and R' substituents comprises a DHT moiety.

2. The conjugate of claim 1, wherein said radionuclide is an Auger electron-emitting radioisotope selected from the group of $^{123}$I, $^{125}$I, $^{77}$Br, $^{80m}$Br, $^{195m}$Hg and $^{113}$Sn.

3. The conjugate of claim 1, wherein said radionuclide is selected from the group of $^{131}$I, $^{32}$P, and $^{225}$At.

4. The conjugate of claim 1, wherein said radionuclide is $^{125}$I.

5. The conjugate of claim 1, having the formula:

6. The conjugate of claim 1 having the formula:

7. The conjugate of claim 1 having the formula:

8. The conjugate of claim 1 having the formula;

9. The conjugate of claim 1 having the formula:

10. A method of treatment of a malignant tumor in a patient in need of such treatment, said tumor comprising cells having androgen receptor, said method comprising administering a therapeutically effective amount of the radiolabeled conjugate of claim 1.

11. The method of claim 10, wherein said cells are prostate cancer cells.

12. The method of claim 10, wherein said cells are ovarian cancer cells.

13. The method of claim 10, wherein said cells are breast cancer cells.

14. The method of claim 10, wherein said radiolabeled conjugate is administered by a method selected from the group consisting of intravenously, intraperitoneally, and intratumor.

15. The method of claim 14, wherein said method of administration is administered intravenously.

16. The method of claim 14, wherein said conjugate is administered periodically for a term of years.

17. The method of claim 16, wherein said conjugate is administered daily.

18. A method for the diagnosis of a malignant tumor in a patient, said tumor comprising cells having androgen receptor, said method comprising administering an effective amount of a radiolabeled conjugate of claim 1, and then imaging the tumor scintigraphically.

* * * * *